United States Patent
Bruestle

(10) Patent No.: US 7,494,469 B2
(45) Date of Patent: Feb. 24, 2009

(54) CONNECTION APPARATUS AND METHOD FOR CONTROLLING AN ULTRASOUND PROBE

(75) Inventor: Reinhold Bruestle, Zipf (AT)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 652 days.

(21) Appl. No.: 10/767,585

(22) Filed: Jan. 29, 2004

(65) Prior Publication Data

US 2005/0154311 A1 Jul. 14, 2005

Related U.S. Application Data

(63) Continuation-in-part of application No. 10/756,231, filed on Jan. 13, 2004, now Pat. No. 7,431,698.

(51) Int. Cl.
*A61B 8/14* (2006.01)

(52) U.S. Cl. .................. 600/459; 600/472; 367/119; 367/153

(58) Field of Classification Search .......... 600/459, 600/472; 367/119, 153; 73/596
See application file for complete search history.

(56) References Cited

U.S. PATENT DOCUMENTS

| | | | |
|---|---|---|---|
| 4,149,419 A | 4/1979 | Connell, Jr. et al. | |
| 4,649,925 A * | 3/1987 | Dow et al. | 600/446 |
| 4,869,257 A | 9/1989 | Molnar et al. | |
| 5,085,221 A * | 2/1992 | Ingebrigtsen et al. | 600/446 |
| 5,127,410 A | 7/1992 | King et al. | |
| 5,186,177 A | 2/1993 | O'Donnell et al. | |
| 5,199,437 A | 4/1993 | Langberg | |
| 5,229,933 A | 7/1993 | Larson, III | |
| 5,368,036 A | 11/1994 | Tanaka et al. | |
| 5,400,790 A | 3/1995 | Pohan et al. | |
| 5,429,136 A | 7/1995 | Milo et al. | |
| 5,435,313 A | 7/1995 | Noda et al. | |
| 5,469,851 A | 11/1995 | Lipschutz | |
| 5,469,852 A | 11/1995 | Nakamura et al. | |
| 5,476,107 A * | 12/1995 | Oakley et al. | 128/897 |
| 5,483,963 A | 1/1996 | Butler et al. | |
| 5,560,362 A * | 10/1996 | Sliwa et al. | 600/439 |
| 5,603,327 A | 2/1997 | Eberle et al. | |
| 5,626,138 A | 5/1997 | Hossack et al. | |
| 5,744,898 A | 4/1998 | Smith et al. | |
| 5,897,501 A | 4/1999 | Wildes et al. | |
| 5,997,479 A | 12/1999 | Savord et al. | |
| 6,007,490 A * | 12/1999 | Pawluskiewicz | 600/459 |
| 6,036,646 A | 3/2000 | Barthe et al. | |
| 6,120,452 A * | 9/2000 | Barthe et al. | 600/459 |
| 6,425,870 B1 * | 7/2002 | Flesch | 600/459 |
| 6,551,248 B2 | 4/2003 | Miller | |
| 6,733,457 B2 * | 5/2004 | Flesch et al. | 600/459 |
| 6,875,178 B2 | 4/2005 | Phelps et al. | |
| 7,022,080 B2 | 4/2006 | Marian, Jr. | |

(Continued)

*Primary Examiner*—Ruth S Smith
*Assistant Examiner*—Parikha S Mehta
(74) *Attorney, Agent, or Firm*—The Small Patent Law Group; Dean D. Small

(57) ABSTRACT

A connection apparatus and method for controlling an ultrasound probe are provided. The ultrasound probe includes a first chamber, a second chamber and a sealing member between the first and second chambers. The ultrasound probe further includes a connection member within the second chamber having a rigid portion and a flexible portion, with the rigid portion forming at least part of the sealing member.

22 Claims, 8 Drawing Sheets

U.S. PATENT DOCUMENTS

| | | | |
|---|---|---|---|
| 2003/0085635 A1* | 5/2003 | Davidsen | 310/334 |
| 2004/0158154 A1 | 8/2004 | Hanafy et al. | |
| 2005/0154312 A1* | 7/2005 | Bruestle | 600/459 |

* cited by examiner

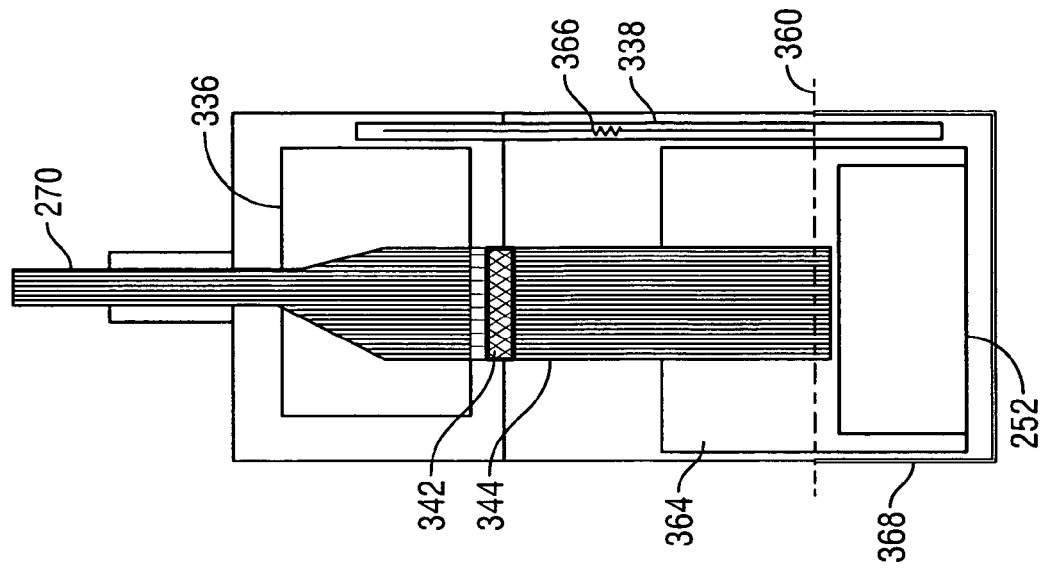
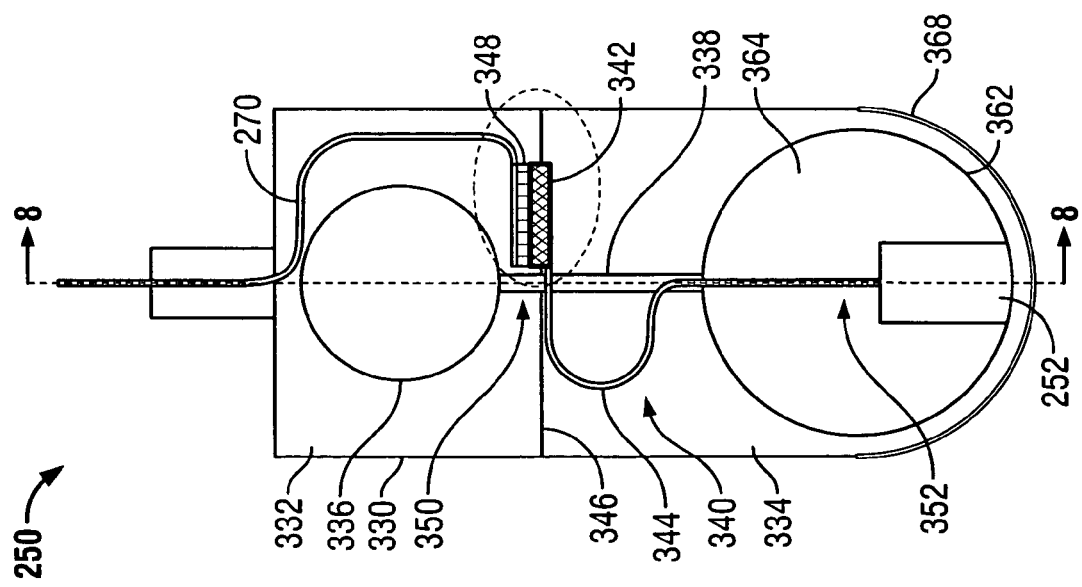

US 7,494,469 B2

CONNECTION APPARATUS AND METHOD FOR CONTROLLING AN ULTRASOUND PROBE

CROSS REFERENCE TO RELATED APPLICATIONS

This application is a continuation-in-part and claims priority to U.S. patent application Ser. No. 10/756,231 filed Jan. 13, 2004 for "APPARATUS AND METHOD FOR CONTROLLING AN ULTRASOUND PROBE," which is hereby incorporated by reference herein in its entirety.

BACKGROUND OF THE INVENTION

This invention relates generally to ultrasound systems and, more particularly, to probes for ultrasound medical imaging systems.

Ultrasound systems typically include ultrasound scanning devices, such as, ultrasound probes having different transducers that allow for performing various different ultrasound scans (e.g., different imaging of a volume or body). The ultrasound probes are typically connected to an ultrasound system for controlling the operation of the probes. The probes include a scan head having a plurality of transducer elements (e.g., piezoelectric crystals), which may be arranged in an array. The ultrasound system drives the transducer elements within the array during operation, such as, during a scan of a volume or body, which may be controlled based upon the type of scan to be performed. The ultrasound system includes a plurality of channels for communicating with the probe. For example, the channels may transmit pulses for driving the transducer elements and for receiving signals therefrom.

In volume probes, wherein the scan head mechanically moves during scan operation, a separate wet and dry chamber are typically provided. In particular, the scan head moves (e.g. rotates) in a sealed wet chamber having an acoustic membrane surrounding a scan head housing that contacts a patient during a scan. The wet chamber is typically filled with an acoustic liquid to allow acoustic coupling during scanning (e.g., during transmissions). The wet chamber is sealed from the dry chamber and may include control components for controlling the operation of the scan head in the wet chamber. The control components communicate with and control the scan head, for example, control the operation of transducer elements within the scan head. The communication between the control components and scan head may be provided by different communication lines (e.g., coaxial or other flexible cable). These communication lines traverse the seal between the wet and dry chambers, requiring the use of sealing members to maintain the liquid tight seal between the chambers. Each sealing member that is required increases the likelihood of a failure, for example, an increased likelihood of liquid leaking into the dry chamber through one of the sealing members. Further, the sealing members add complexity in design and cost to the probe. For example, additional components (e.g., brackets) between the wet and dry chambers may be needed to maintain the position and sealing engagement of the sealing members.

BRIEF DESCRIPTION OF THE INVENTION

In one exemplary embodiment, an ultrasound probe is provided. The ultrasound probe includes a first chamber, a second chamber and a sealing member between the first and second chambers. The ultrasound probe further includes a connection member within the second chamber having a rigid portion and a flexible portion, with the rigid portion forming at least part of the sealing member.

In another exemplary embodiment, a method for controlling an ultrasound probe is provided. The method includes communicating between at least one transducer array and a host system via a connection member, with the connection member formed of a rigid portion and a flexible portion. The flexible portion is configured to connect to the at least one transducer array and the rigid portion forms at least part of a wall between a wet chamber having the at least one transducer array therein and a dry chamber having a system cable therein. The rigid portion is also configured to connect to the system cable, with the system cable connected to the host system. The method further includes controlling elements of the at least one transducer array with the communicating.

BRIEF DESCRIPTION OF THE DRAWINGS

FIG. 7 is a cross-sectional elevation view of a probe in accordance with an exemplary embodiment of the present invention.

FIG. 8 is an elevation view taken along the line 8-8 of FIG. 7.

DETAILED DESCRIPTION OF THE INVENTION

Exemplary embodiments of ultrasound systems and methods for controlling ultrasound probes are described in detail below. In particular, a detailed description of exemplary ultrasound systems will first be provided followed by a detailed description of various embodiments of methods and systems for controlling ultrasound probes. A technical effect of the various embodiments of the systems and methods described herein include at least one of improving the sealing arrangement between chambers of an ultrasound probe and allowing for easier maintenance and assembly of the ultrasound probe.

Figure 1:
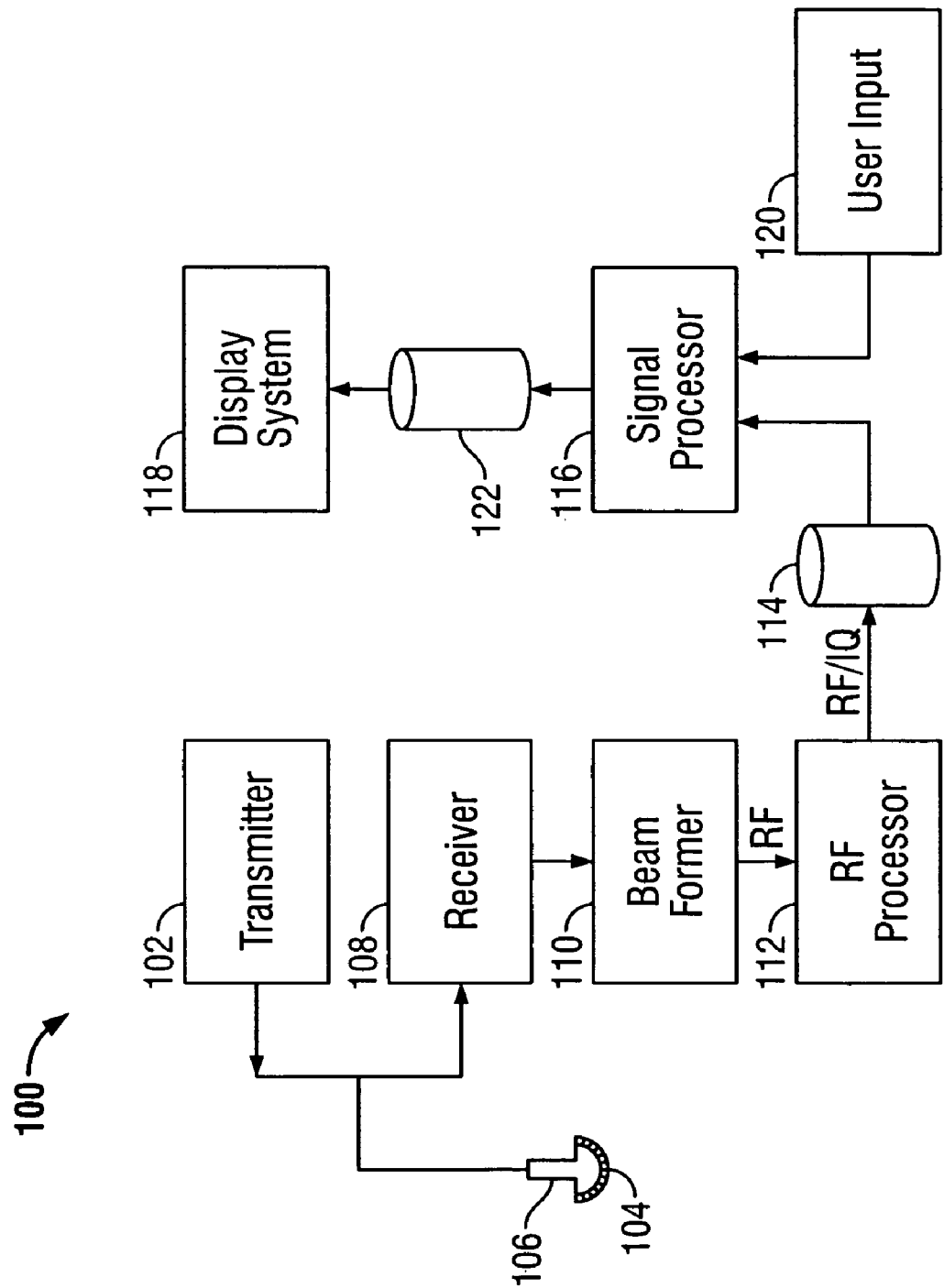
FIG. 1 is a block diagram of an ultrasound system in accordance with one exemplary embodiment of the present invention.

FIG. 1 illustrates a block diagram of an exemplary embodiment of an ultrasound system 100 that may be used, for example, to acquire and process ultrasonic images. The ultrasound system 100 includes a transmitter 102 that drives an array of elements 104 (e.g., piezoelectric crystals) within or formed as part of a transducer 106 to emit pulsed ultrasonic signals into a body or volume. A variety of geometries may be used and one or more transducers 106 may be provided as part of a probe (not shown). The pulsed ultrasonic signals are back-scattered from density interfaces and/or structures, for example, in a body, like blood cells or muscular tissue, to produce echoes that return to the elements 104. The echoes are received by a receiver 108 and provided to a beamformer 110. The beamformer performs beamforming on the received echoes and outputs an RF signal. The RF signal is then processed by an RF processor 112. The RF processor 112 may include a complex demodulator (not shown) that demodulates the RF signal to form IQ data pairs representative of the echo signals. The RF or IQ signal data then may be routed directly to an RF/IQ buffer 114 for storage (e.g., temporary storage).

The ultrasound system 100 also includes a signal processor 116 to process the acquired ultrasound information (i.e., RF signal data or IQ data pairs) and prepare frames of ultrasound information for display on a display system 118. The signal processor 116 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in the RF/IQ buffer 114 during a scanning session and processed in less than real-time in a live or off-line operation.

The ultrasound system 100 may continuously acquire ultrasound information at a frame rate that exceeds fifty frames per second, which is the approximate perception rate of the human eye. The acquired ultrasound information is displayed on the display system 118 at a slower frame-rate. An image buffer 122 may be included for storing processed frames of acquired ultrasound information that are not scheduled to be displayed immediately. In an exemplary embodiment, the image buffer 122 is of sufficient capacity to store at least several seconds of frames of ultrasound information. The frames of ultrasound information may be stored in a manner to facilitate retrieval thereof according to their order or time of acquisition. The image buffer 122 may comprise any known data storage medium.

A user input device 120 may be used to control operation of the ultrasound system 100. The user input device 120 may be any suitable device and/or user interface for receiving user inputs to control, for example, the type of scan or type of transducer to be used in a scan.

Figure 2:
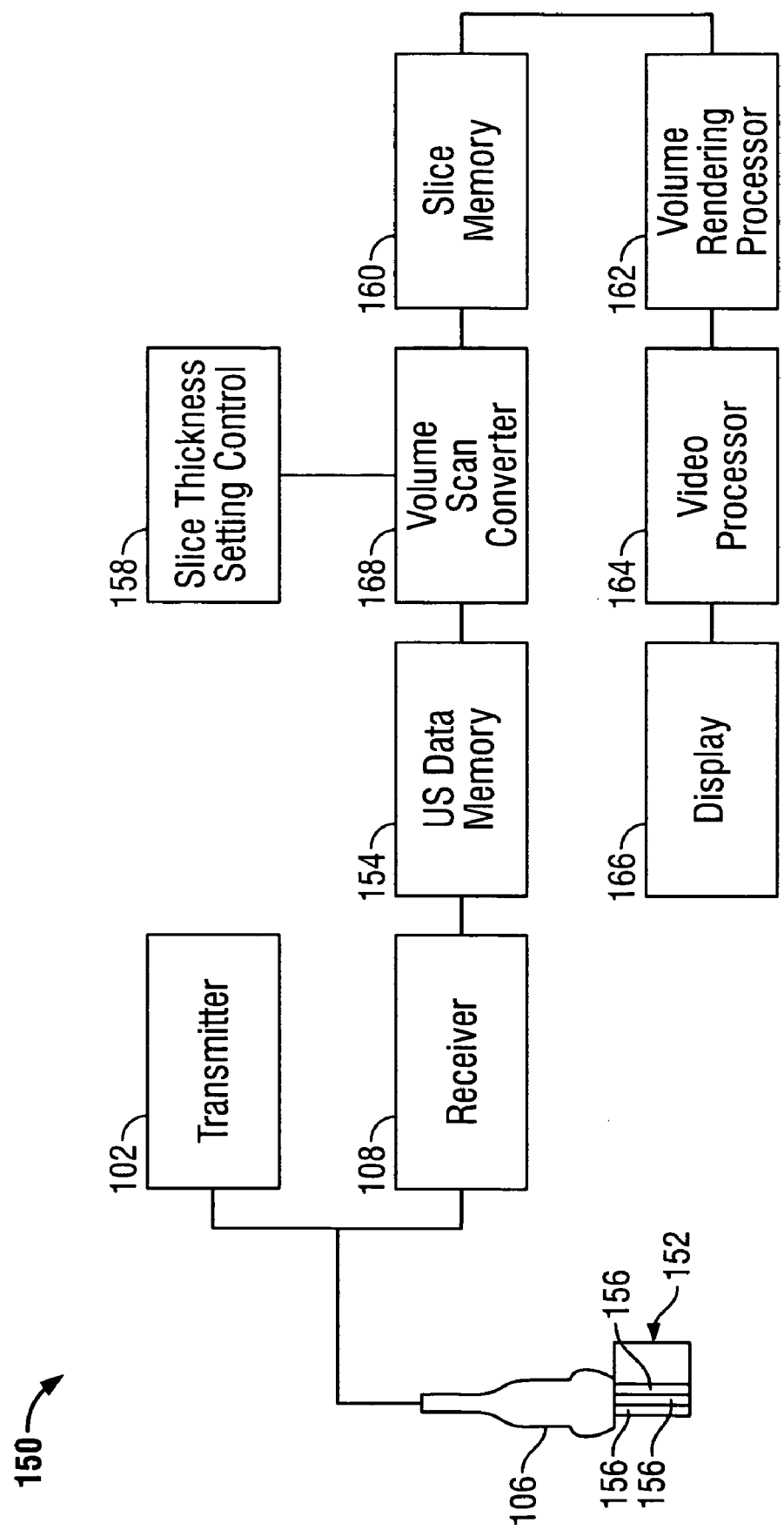
FIG. 2 is a block diagram of an ultrasound system in accordance with another exemplary embodiment of the present invention.

FIG. 2 illustrates a block diagram of another exemplary embodiment of an ultrasound system 150 that may be used, for example, to acquire and process ultrasonic images. The ultrasound system 150 includes the transducer 106 in communication with the transmitter 102 and receiver 108. The transducer 106 transmits ultrasonic pulses and receives echoes from structures inside a scanned ultrasound volume 152. A memory 154 stores ultrasound data from the receiver 108 derived from the scanned ultrasound volume 152. The scanned ultrasound volume 152 may be obtained by various techniques, including, for example, 3D scanning, real-time 3D imaging, volume scanning, scanning with transducers having positioning sensors, freehand scanning using a Voxel correlation technique, 2D scanning or scanning with a matrix of array transducers, among others.

The transducer 106 is moved, such as along a linear or arcuate path, while scanning a region of interest (ROI). At each linear or arcuate position, the transducer 106 obtains a plurality of scan planes 156. The scan planes 156 are collected for a thickness, such as from a group or set of adjacent scan planes 156. The scan planes 156 are stored in the memory 154, and then provided to a volume scan converter 168. In some exemplary embodiments, the transducer 106 may obtain lines instead of the scan planes 156, with the memory 154 storing lines obtained by the transducer 106 rather than the scan planes 156. The volume scan converter 168 receives a slice thickness setting from a slice thickness setting control 158, which identifies the thickness of a slice to be created from the scan planes 156. The volume scan converter 168 creates a data slice from multiple adjacent scan planes 156. The number of adjacent scan planes 156 that are obtained to form each data slice is dependent upon the thickness selected by the slice thickness setting control 158. The data slice is stored in a slice memory 160 and accessed by a volume rendering processor 162. The volume rendering processor 162 performs volume rendering upon the data slice. The output of the volume rendering processor 162 is provided to a video processor 164 that processes the volume rendered data slice for display on a display 166.

It should be noted that the position of each echo signal sample (Voxel) is defined in terms of geometrical accuracy (i.e., the distance from one Voxel to the next) and one or more ultrasonic responses (and derived values from the ultrasonic response). Suitable ultrasonic responses include gray scale values, color flow values, and angio or power Doppler information. It should be noted that the ultrasound system 150 also may include a user input or user interface for controlling the operation of the ultrasound system 150.

It should be noted that the ultrasound systems 100 and 150 may include additional or different components. For example, the ultrasound system 150 may include a user interface or user input 120 (shown in FIG. 1) to control the operation of the ultrasound system 150, including, to control the input of patient data, scan parameters, a change of scan mode, and the like.

Figure 3:
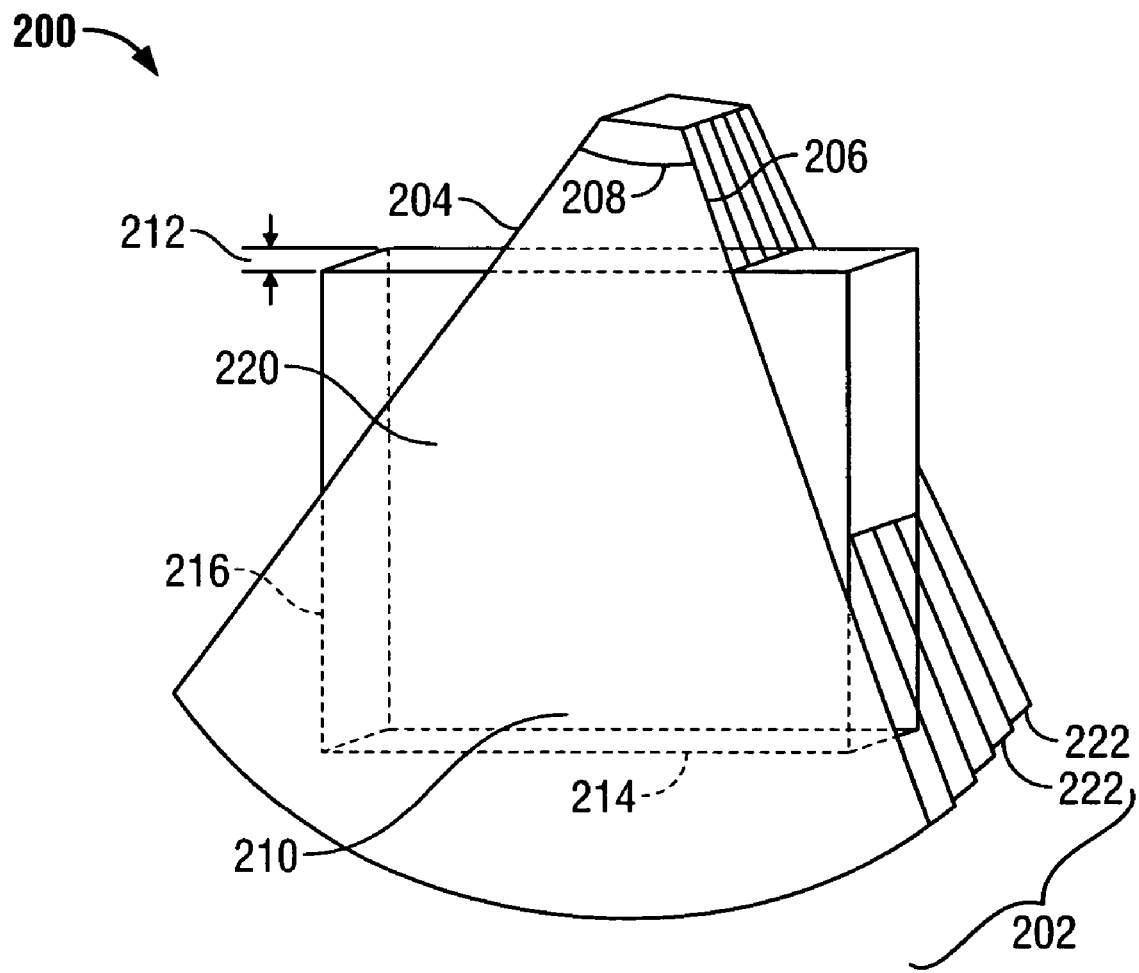
FIG. 3 is a perspective view of an image of an object acquired by the systems of FIGS. 1 and 2 in accordance with an exemplary embodiment of the present invention.

FIG. 3 illustrates an exemplary image of an object 200 that may be acquired by the ultrasound systems 100 and 150. The object 200 includes a volume 202 defined by a plurality of sector shaped cross-sections with radial borders 204 and 206 diverging from one another at an angle 208. The transducer 106 (shown in FIGS. 1 and 2) electronically focuses and directs ultrasound firings longitudinally to scan along adjacent scan lines in each scan plane 156 (shown in FIG. 2) and electronically or mechanically focuses and directs ultrasound firings laterally to scan adjacent scan planes 156. The scan planes 156 obtained by the transducer 106, and as illustrated in FIG. 1, are stored in the memory 154 and are scan converted from spherical to Cartesian coordinates by the volume scan converter 168. A volume comprising multiple scan planes 156 is output from the volume scan converter 168 and stored in the slice memory 160 as a rendering region 210. The rendering region 210 in the slice memory 160 is formed from multiple adjacent scan planes 156.

The rendering region 210 may be defined in size by an operator using a user interface or input to have a slice thickness 212, width 214 and height 216. The volume scan converter 168 (shown in FIG. 2) may be controlled by the slice thickness setting control 158 (shown in FIG. 2) to adjust the thickness parameter of the slice to form a rendering region 210 of the desired thickness. The rendering region 210 defines the portion of the scanned ultrasound volume 152 that is volume rendered. The volume rendering processor 162 accesses the slice memory 160 and renders along the slice thickness 212 of the rendering region 210.

Referring now to FIGS. 1 and 2, during operation, a slice having a pre-defined, substantially constant thickness (also referred to as the rendering region 210) is determined by the slice thickness setting control 158 and is processed in the volume scan converter 168. The echo data representing the rendering region 210 (shown in FIG. 3) may be stored in the slice memory 160. Predefined thicknesses between about 2 mm and about 20 mm are typical, however, thicknesses less than about 2 mm or greater than about 20 mm may also be suitable depending on the application and the size of the area to be scanned. The slice thickness setting control 158 may include a control member, such as a rotatable knob with discrete or continuous thickness settings.

The volume rendering processor 162 projects the rendering region 210 onto an image portion 220 of an image plane(s) 222 (shown in FIG. 3). Following processing in the volume rendering processor 162, pixel data in the image portion 220 may be processed by the video processor 164 and then displayed on the display 166. The rendering region 210 may be located at any position and oriented at any direction within the volume 202. In some situations, depending on the size of the region being scanned, it may be advantageous for the rendering region 210 to be only a small portion of the volume 202.

Figure 4:
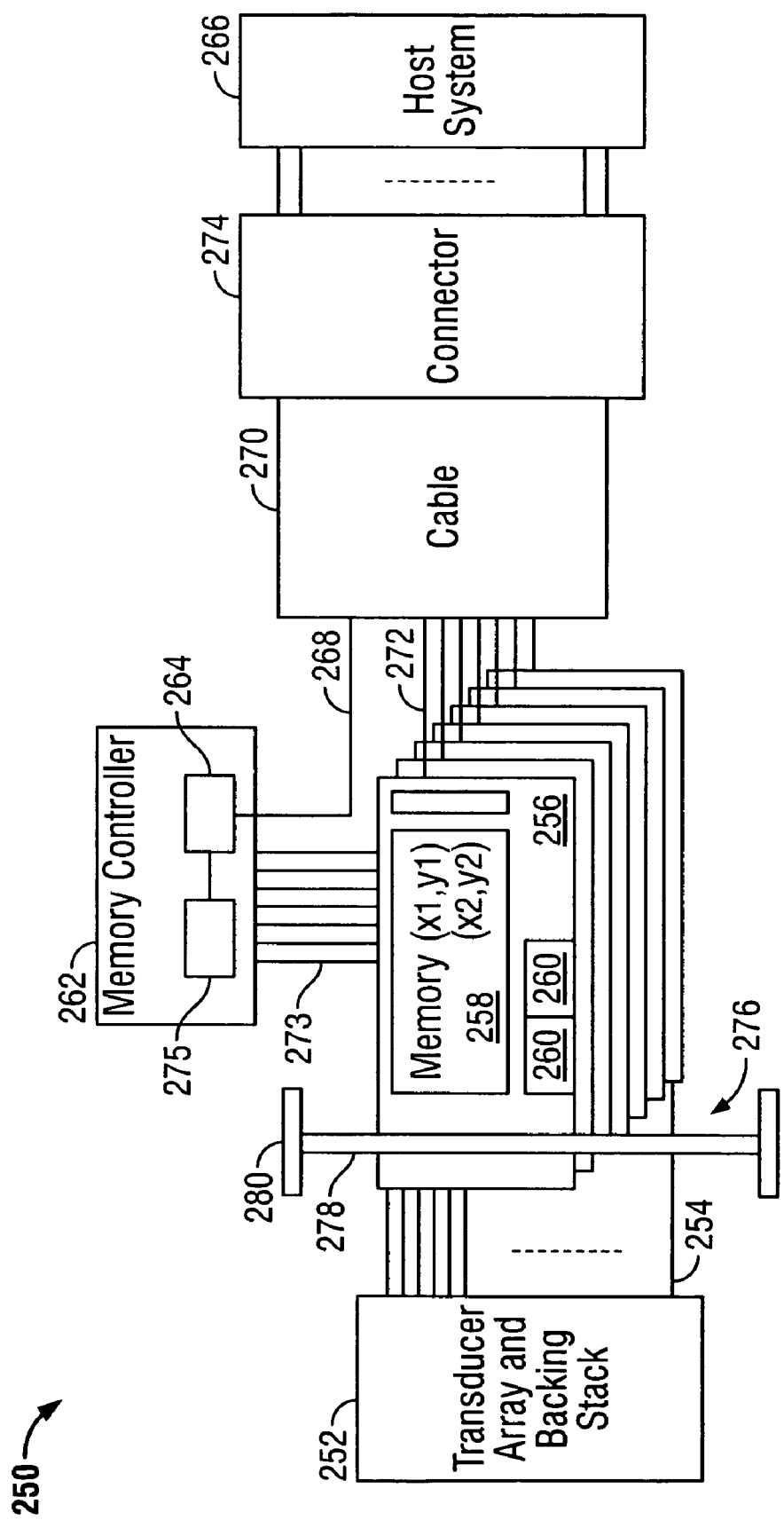
FIG. 4 is a block diagram of an ultrasound probe in communication with a host system in accordance with an exemplary embodiment of the present invention.

FIG. 4 illustrates a block diagram of an exemplary embodiment of an ultrasound probe 250 that may be used in connection with the ultrasound systems 100 or 150. The ultrasound probe 250 includes a transducer array and backing stack 252 (the "transducer array 252"), transducer flex cables 254, which may be formed as a scan head cable, and multiple processing boards 256 that support processing electronics. Each processing board 256 may includes a location memory 258 (which may include geometry RAM, encoder RAM, location registers and control registers as noted below) and signal processors 260. A location memory controller 262 (e.g., a general purpose CPU, microcontroller, PLD, or the like) also may be provided and includes a communication interface 264.

The communication interface 264 establishes data exchange with a host system 266 over communication lines 268 (e.g., digital signal lines) and through a system cable 270. Additionally, in an exemplary embodiment, the system cable 270 includes coaxial cables 272 that connect to the processing boards 256 to communicate transmit pulse waveforms to the transducer array 252 and communicate receive signals, after beamforming, to the host system 266. The probe 250 also may include a connector 274, through which the probe 250 connects to the host system 266.

A clamp 276 may be provided to hold the transducer flex cables 254 against the processing boards 256. The clamp 276 thereby aids in establishing electrical connectivity between the transducer flex cables 254 and the processing boards 256. The clamp 276 may include a dowel pin 278 and a bolt 280, although other implementations are also suitable.

The transducer array 252 is bonded onto the backing stack, as will be described in more detail below with regard to FIG. 5. The transducer flex cables 254 provide electrical signal connections through the backing stack. In one exemplary embodiment, there are forty-two transducer flex cables 254, each with fifty signal connections. Thus, the transducer flex cables 254 support transmit and receive signal connections for as many as 2100 transducer elements in the transducer array 252, although fewer may be used. For example, each processing board 256 may couple to six transducer flex cables 254, and thereby includes signal connections for 300 transducer elements.

The processing boards 256 may, like the flex cables 254, be formed from a flex material, such as, for example, polyimide, polyester, etc. The processing boards 256 include the processing electronics for the transducer array 252, including the signal processors 260 that perform beamforming on the receive apertures in the transducer array 252.

Each signal processor 260 may handle, for example, four receive apertures defined at selected spatial locations on the transducer array 252. The receive apertures may be triangular apertures that include fifteen acoustic transducer elements arranged, for example, as a row of five elements above a row of four elements above a row of three elements above a row of two elements above a row of one element. Furthermore, each processing board 256 may include five signal processors 260. Thus, in the receive direction, each processing board 256 may process twenty receive apertures, each including fifteen acoustic transducer elements.

For every ultrasound beam, the location memory controller 262 connects via digital signal lines 273 (e.g., carried by a separate flex cable) to each location memory 258 on each processing board 256. The location memory controller 262 communicates the spatial location information into each location memory 258 for each receive aperture processed by the signal processors 260 on the processing boards 256. The digital signal lines 273 may include, for example, a clock line for each processing board 256, a serial command data line for each processing board 256, two data lines (for a total of fourteen data lines) connected to each processing board 256, an output enable for one or more of the signal processors 260, and a test signal.

The location memory controller 262 communicates with the host system 266 over the digital signal lines 273 that may form part of, for example, a synchronous serial port. To that end, the communication interface 264 and digital signal lines 273 may implement a low voltage differential signal interface, for example, including a coaxial cable with a grounded shield and center signal wire. The location memory controller 262 includes a block of cache memory 275, for example, 1-8 MBytes of static random access memory (SRAM).

Figure 5:
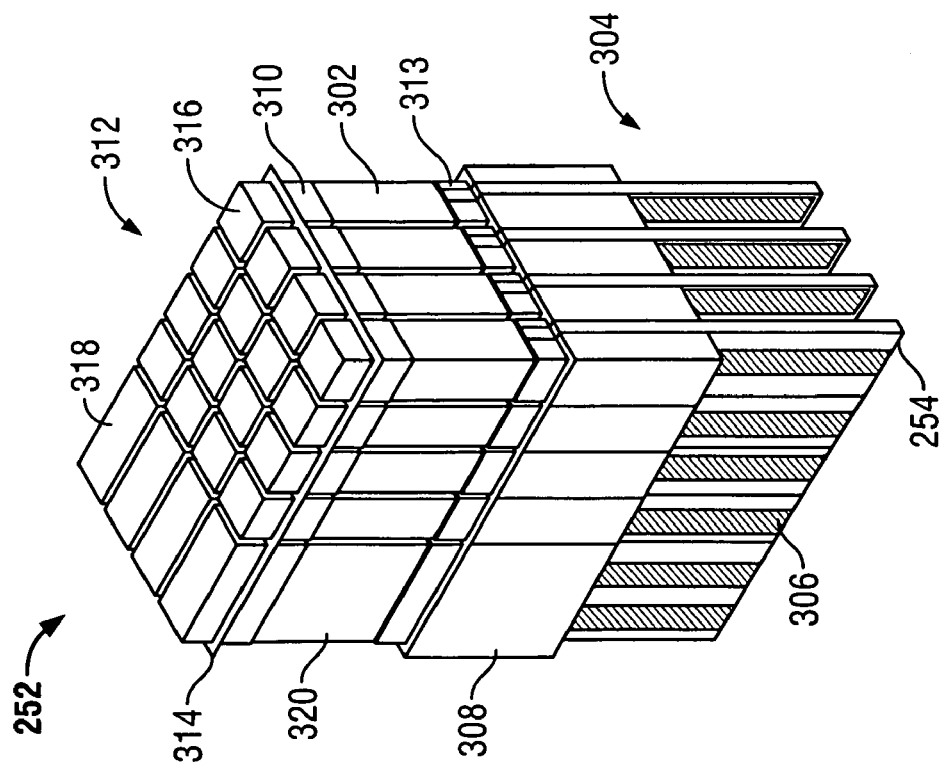
FIG. 5 is a perspective view of an exemplary transducer stack including an array of transducer elements that may be used in the ultrasound probe shown in FIG. 4.

FIG. 5 shows one exemplary embodiment of the transducer array 252. The transducer array 252 includes piezoelectric ceramic 302 that converts electrical-to-acoustic and acoustic-to-electrical energy. The piezoelectric ceramic 302 is located within the center of the transducer array 252. On the signal side, the piezoelectric ceramic 302 is attached to a z-axis backing block 304 comprised of alternating layers of transducer flex cables 254 and acoustic absorbing material 308 bonded into the solid backing block 304.

The backing block 304 is cut in a direction perpendicular to the orientation of the transducer flex cables 254 thereby exposing the ends of the individual transducer flex cable 254 circuit traces 306 to provide for high density signal connection. The ceramic 302, an electrically conductive inner acoustic matching layer 310 (e.g., a metal filled graphite such as Antimony-Graphite), and the top surface of the backing block 304 are diced in one operation to form discrete acoustic transducer elements 312 centered over each of the flex circuit traces 306 in the transducer flex cables 254. Thus, there is a signal plane 313 on the z-axis backing block 304.

Each circuit trace 306 contacts the bottom, or signal side, of one transducer element 312. A ground metal layer 314 is coated onto one side of the outer acoustic matching layer 316, which may be formed from a plastic. This matching layer 316 is attached to the top of each element 312 to form a ground connection across the face of the transducer array 252. The outer matching layer 316 is partially diced to separate it into discrete elements, thereby improving the acceptable angle of the transducer element 312. In one exemplary embodiment, however, the dicing does not penetrate to the ground metal layer 314.

The electrical ground connection to each transducer element 312 is made via the outermost elements 318 in the transducer. A wraparound ground 320 on the ceramic 302 is also provided. Once the transducer array 252 is mounted into a scan head or head shell, a thin silicone protective facing may be applied.

Figure 6:
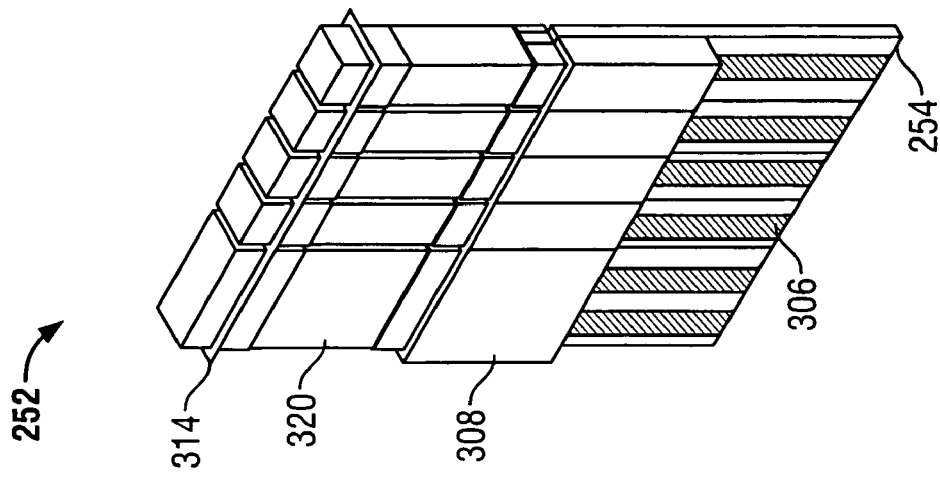
FIG. 6 is a perspective view of another exemplary transducer stack including an array of transducer elements that may be used in the ultrasound probe shown in FIG. 4.

It should be noted that different transducer arrays that may have different interconnections may be used as desired or needed (e.g., based upon the probe type or application). For example, FIG. 5 shows an interconnection configuration suitable for arrays requiring an electrical interface of very high density (e.g., two-dimensional (2D) arrays). However, other types of arrays, for example, one-dimensional (1D) arrays, do not require electrical interfaces of this high density and other interconnection configurations may be more suitable. For example, as shown in FIG. 6, in a 1D array application, the 1D array includes a single transducer flex cable 254 wherein the circuit traces 306 contact the elements of the transducer array 252. The elements of the transducer array 252 are positioned adjacent each other as the circuit traces 306 on the transducer flex cable 254 are positioned adjacent each other. Similar configurations with a single transducer flex cable 254 may be used, for example, with 1.25D, 1.5D or 1.75D arrays.

FIGS. 7 and 8 illustrate an exemplary embodiment of the probe 250, and in particular, a volume imagining probe, having a transducer array 252 in communication with a host system 266 (shown in FIG. 4). The probe 250 includes a housing 330 having a first chamber 332 (e.g., a dry chamber) and a second chamber 334 (e.g., a wet chamber). The first chamber 332 and second chamber 334 may be formed as a single unit (e.g., unitary construction) or may be formed as separate units connected together (e.g. modular design). In an exemplary embodiment, the first chamber 332 is a dry or air chamber having contained therein drive means for mechanically controlling the transducer array 252 and communication means for electrically controlling the transducer array 252. The drive means generally includes a motor 336 (e.g., stepper motor) and a gear arrangement 338, such as a two-stage gear arrangement having a belt drive and a rope drive. The communication means generally includes the system cable 270 that communicates with the host system 266 to drive the elements of the transducer array 252 (e.g., selectively activate the elements of the transducer array 252).

It should be noted that although the drive means and communication means are described herein having specific component parts, they are not so limited. For example, the drive means may have a different gear arrangement and the communication means may have different connection members or transmission lines.

In this exemplary embodiment, the second chamber 334 is a wet chamber (e.g., chamber having acoustic liquid therein) having contained therein transducer driving means for moving (e.g., rotating) the transducer array 252 and transducer control means for selectively driving elements of the transducer array 252 (e.g., the piezoelectric ceramics 302). The transducer driving means generally includes a drive shaft 360 in connection with a scan head housing 362, supported, for example, on brackets (not shown), that operates to move the transducer array 252 as part of a scan head 364 when driven by the drive means. A support member (not shown) also may be provided for supporting the scan head housing 362 and a biasing spring 366 may be provided, for example, to ensure proper tension on the drive means and transducer drive means. It should be noted that an acoustic membrane 368 may be provided surrounding the scan head housing 362 and formed as part of the housing 330.

The transducer control means generally includes a connection member 340 having one or more communication lines for connecting the system cable 270 and the transducer array 252, and providing communication therebetween. In one exemplary embodiment, the connection member 340 is formed from a printed circuit board having a rigid portion 342 (e.g., rigid printed circuit board portion) and a flexible portion 344 (e.g., flexible printed circuit board portion). However, it should be noted that the connection member 340 may be formed of any suitable material and/or component parts as desired or needed. In general, the rigid portion 342 and the flexible portion 344 are formed to have a flexibility/rigidity as desired or needed, for example, based upon the type of probe or application. For example, the elastic modulus or mean elastic modulus of the rigid portion 342 and the flexible portion 344 may be determined by the wiring layout of the printed circuit board portion as a result of the distribution of metal layers on the printed circuit board, which may be selected based upon the type of probe. Thus, the material flexibility/rigidity of the rigid portion 342 and flexible portion 344 may be varied as desired or needed. In general, the rigid portion 342 is formed such that it provides sufficient stability from it's stiffness or rigidity (e.g., rigid printed circuit board portion) to ensure proper sealing and/or functioning of a probe (e.g., fluid impervious seal between the first chamber 332 and the second chamber 334). In general, the flexible portion 344 is formed such that it provides sufficient flexibility and durability to ensure proper functioning and/or operation of a probe (e.g., to ensure proper and reliable interconnection between the rigid portion 342 and a moving transducer array 252).

The rigid portion 342 forms part of a sealing member 346, such as, for example, a wall (e.g., fluid impervious wall) between the first chamber 332 and second chamber 334. The rigid portion 342 may be integrally formed with the sealing member 346 or may be provided in sealing engagement therewith, for example, using adhesive sealing (e.g., epoxy) or other sealing members (e.g., O-rings). In the various exemplary embodiments, the rigid portion 342 and sealing member 346 are a single unitary structure. It should be noted that additional members (e.g., brackets) may be provided in connection with the sealing member 346 to provide mechanical stability for bearing mechanical loads that may be applied to the rigid portion 342 and provide additional pressure on the sealing member 346. For example, a mechanical load may be applied to the rigid portion 342 by the flexible portion 344 or an interconnection member 348. The mechanical load may result, for example, from the movement of the flexible portion 344 as described herein, by a differential pressure between the first chamber 332 and second chamber 334, and by tensions of the system cable 270 that are induced into the rigid portion 342 via the interconnection member 348, among others.

At a first portion 350 (e.g., first end) of the connection member 340, the rigid portion 342 is connected via the interconnection member 348 (e.g., board-to-board connector) to the system cable 270. At a second portion 352 (e.g., second end) of the connection member 340, the flexible portion 344 is connected to the transducer array 252. It should be noted that additional or different connectors may be used to connect to the first portion 350 and second portion 352. The connection member 340 thereby provides communication between the transducer array 252 and the host system 266 via the system cable 270. However, additional or different control members may be provided, such as, for example, multiplexing circuits connected to the transducer array 252 for controlling the operation of the elements of the transducer array 252.

It should be noted that although the transducer driving means and transducer control means are described herein having specific component parts, they are not so limited. For example, the transducer driving means may have a different shaft arrangement and the transducer control means may have different control circuits or transmission lines. It also should be noted that additional or different component parts may be provided in connection with the probe 250 as needed or desired, and/or based upon the particular type and application of the probe 250. For example, a lens covering the transducer array 252 may be provided based upon the type of probe 250.

Figure 9:
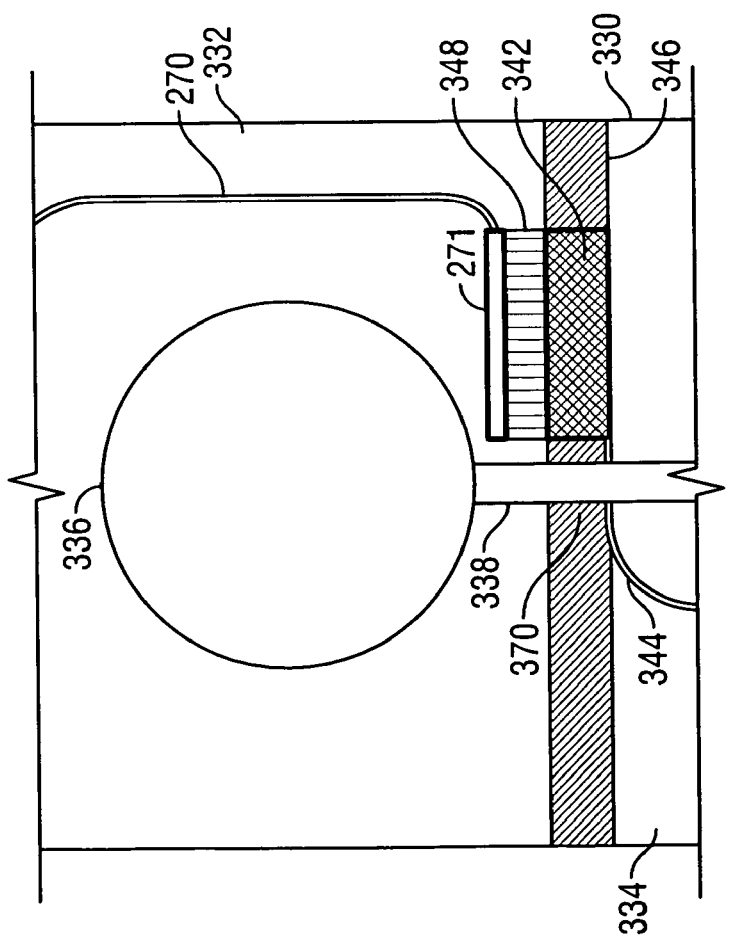
FIG. 9 is a partial cross-sectional elevation view of an ultrasound probe in accordance with an exemplary embodiment of the present invention showing a rigid portion of a connection member forming part of a wall between chambers of the ultrasound probe.

In an exemplary embodiment, and as shown in FIG. 9, the first chamber 332 and second chamber 334 are separated by the sealing member 346 (e.g., fluid impervious wall), with the rigid portion 342 forming a part of the sealing member 346. The sealing member 346 provides a liquid tight sealing arrangement between the first chamber 332 and the second chamber 334 and may be integrally formed as part of one of the first and second chambers 332 and 334. One or more slots or openings 370 may be provided as part of the sealing member 346 to allow for passage therethrough, for example, of a portion of the drive means (e.g., rope portion of a rope drive). The slots or openings 370 are sealed, for, example, with a sealing gasket, epoxy or other suitable sealing member to ensure proper sealing between the first chamber 332 and second chamber 334. It should be noted that the system cable 270 may include a connector end 271 for connection to the interconnection member 348.

Figure 10:
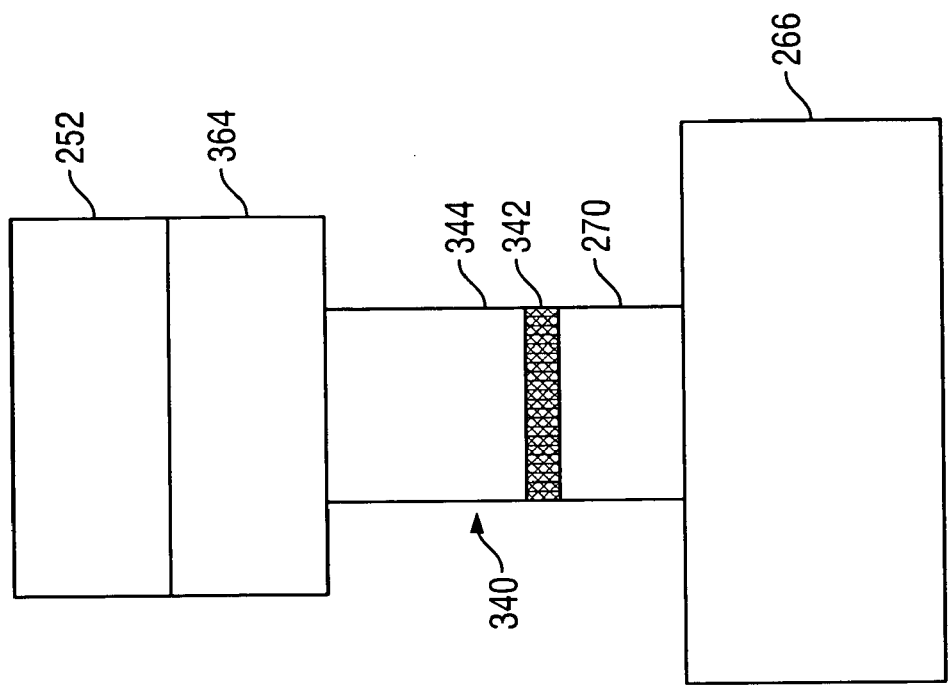
FIG. 10 is a block diagram showing a connection arrangement for an ultrasound probe in accordance with an exemplary embodiment of the present invention.

Thus, as shown in FIG. 10, the transducer array 252 is connected via the connection member 340 to the system cable 270. Specifically, the flexible portion 344 connects to the transducer array 252 and the rigid portion 342 connects to the system cable 270. The system cable 270 then connects to the host system 266.

Figure 11:
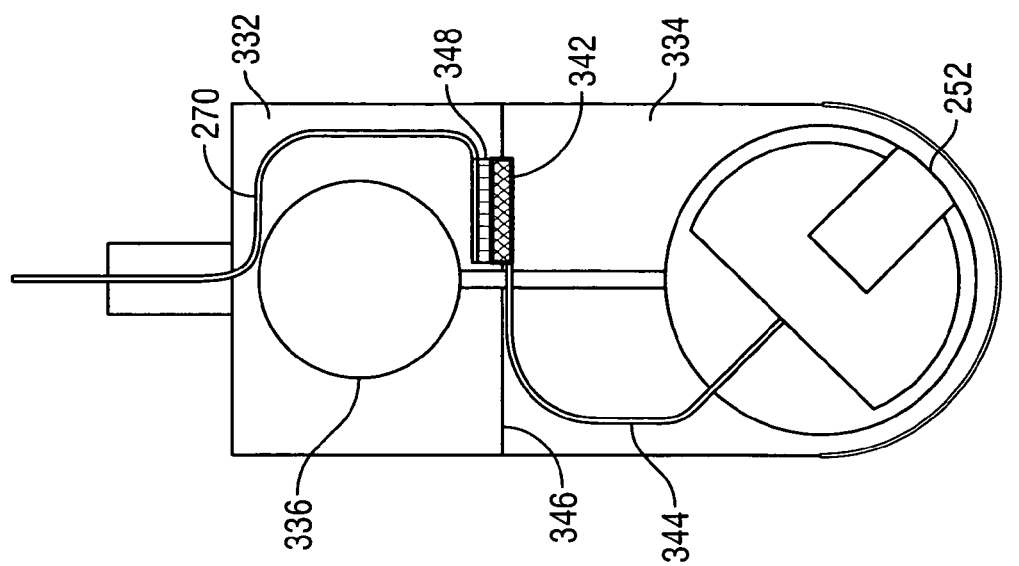
FIGS. 11-13 are cross-sectional elevation views of an ultrasound probe in accordance with an exemplary embodiment of the present invention showing a moving scan head.
Figure 12:
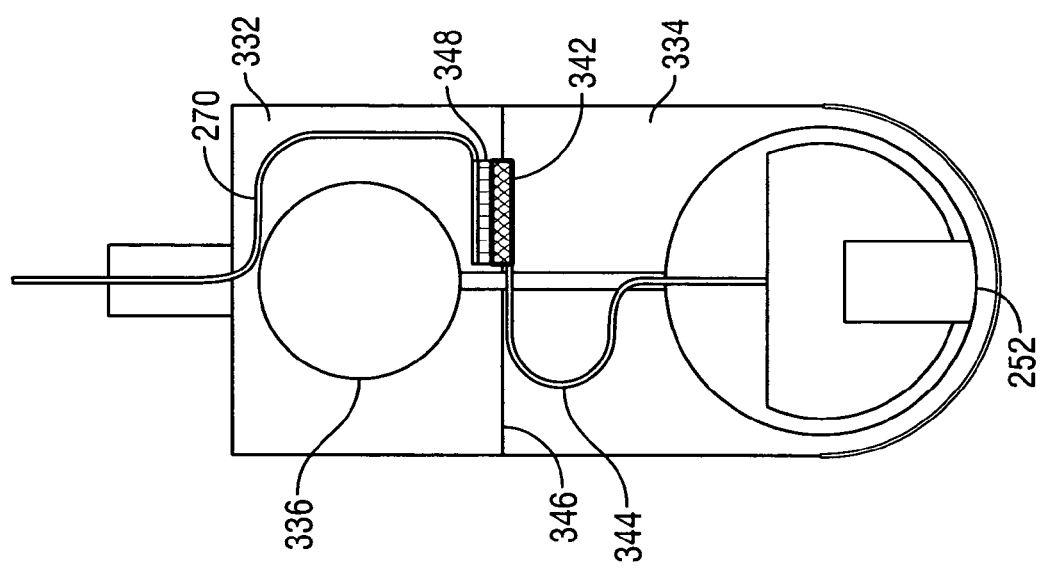
Figure 13:
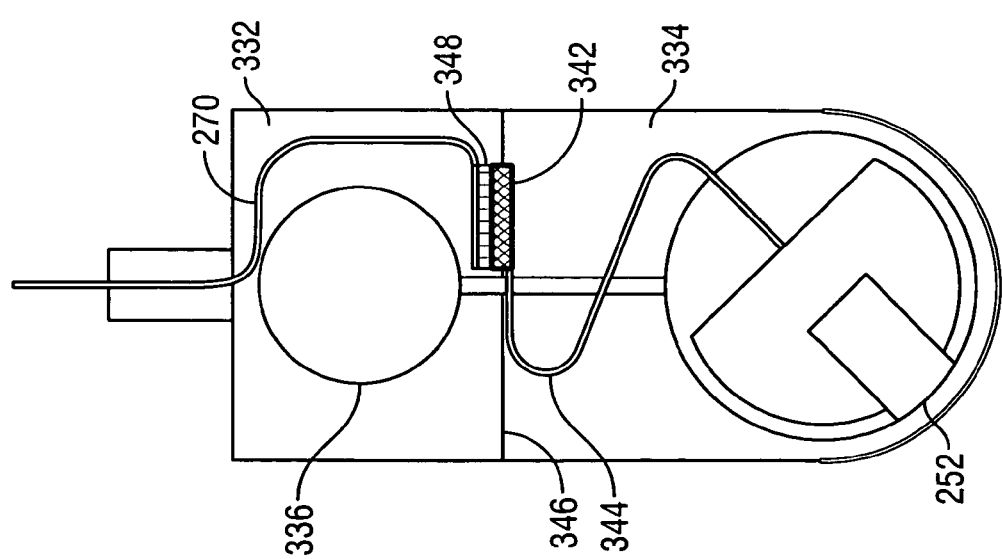

The connection member 340 allows for communication with and control of the operation of the elements of a moving transducer array 252 (e.g., selectively driving the elements of the transducer array 252) as shown in FIGS. 11-13. The connection member 340 also provides an improved sealing arrangement and more modular probe design (e.g., two chambers removably connectable). It should be noted that the transducer array 252 may be configured for operation in different modes, such as, for example, a 1D, 1.25D, 1.5D, 1.75D and 2D mode of operation.

While the invention has been described in terms of various specific embodiments, those skilled in the art will recognize that the invention can be practiced with modification within the spirit and scope of the claims.

What is claimed is:

1. An ultrasound probe comprising:
    a first chamber;
    a second chamber; and
    a sealing member between the first and second chambers, wherein the second chamber includes only a single connection member, the single connection member being only within the second chamber and having a rigid portion and a flexible portion, the rigid portion forming at least part of the sealing member and wherein the connection member comprises a printed circuit board.

2. An ultrasound probe in accordance with claim 1 wherein the sealing member comprises a wall between the first and second chambers.

3. An ultrasound probe in accordance with claim 1 wherein the first chamber is a dry chamber and the second chamber is a wet chamber.

4. An ultrasound probe in accordance with claim 1 wherein the rigid portion comprises a rigid printed circuit board and the flexible portion comprises a flexible printed circuit board.

5. An ultrasound probe in accordance with claim 1 wherein the rigid portion is configured to connect to a system cable in the first chamber and the flexible portion is configured to connect to a transducer array in the second chamber, the transducer array provided as part of a scan head configured to move within the second chamber.

6. An ultrasound probe in accordance with claim 1 wherein the rigid portion is integrally formed with the sealing member.

7. An ultrasound probe in accordance with claim 1 wherein the rigid portion is sealingly engaged with the sealing member.

8. An ultrasound probe in accordance with claim 1 further comprising an interconnection member to connect the rigid portion to a system cable within the first chamber.

9. An ultrasound probe in accordance with claim 1 wherein the sealing member comprises at least one opening.

10. An ultrasound probe in accordance with claim 1 wherein the first and second chambers are formed in a unitary construction.

11. An ultrasound probe in accordance with claim 1 wherein the first and second chambers are formed in a modular construction.

12. An ultrasound probe in accordance with claim 1 wherein the ultrasound probe is configured to operate in at least one of a 1D, 1.25D, 1.5D, 1.75D and 2D mode of operation.

13. An ultrasound probe comprising:
    a transducer array;
    a first chamber;
    a second chamber; and
    a sealing member between the first and second chambers, wherein the second chamber includes only a single connection member, the single connection member being only within the second chamber and having a rigid portion and a flexible portion, the rigid portion forming at least part of the sealing member, wherein the rigid portion is configured to connect to a system cable in the first chamber and the flexible portion is configured to connect to the transducer array in the second chamber.

14. An ultrasound probe comprising:
    at least one transducer;
    a dry chamber having drive means for mechanically controlling the at least one transducer and communication means for electrically controlling the at least one transducer; and
    a wet chamber having a connection member formed of a rigid portion and a flexible portion, the rigid portion forming at least part of a wall between the wet and dry chambers and configured to connect to the communication means, and the flexible portion configured to connect to the at least one transducer.

15. An ultrasound probe in accordance with claim 14 wherein the communication means comprises a system cable.

16. An ultrasound probe in accordance with claim 14 wherein the drive means comprises a motor and gear arrangement.

17. An ultrasound probe in accordance with claim 14 wherein the connection member further comprises a printed circuit board.

18. An ultrasound probe in accordance with claim 14 wherein the dry and wet chambers are configured to connect in a modular arrangement.

19. A connection member for an ultrasound probe, the connection member comprising:
  a wet chamber;
  a dry chamber;
  at least one transducer in the wet chamber;
  a flexible portion within only the wet chamber configured to connect to the at least one transducer; and
  a rigid portion forming at least part of a sealing member between the wet chamber and the dry chamber, the rigid portion configured to connect to a system cable in the dry chamber, the flexible and rigid portions being a single member.

20. A connection member in accordance with claim 19 wherein the flexible portion and rigid portion each comprise a printed circuit board.

21. A method for controlling an ultrasound probe, the method comprising:
  communicating between at least one transducer array and a host system via a connection member, the connection member comprising a rigid portion and a flexible portion that form a single member, the flexible portion being entirely within a wet chamber and configured to connect to the at least one transducer array, the rigid portion forming at least part of a wall between the wet chamber having the at least one transducer array therein and a dry chamber having a system cable therein, the rigid portion configured to connect to the system cable, with the system cable connected to the host system; and
  controlling elements of the at least one transducer array with the communicating.

22. A method in accordance with claim 21 wherein the connection member comprises a printed circuit board.

* * * * *